US010179196B2

(12) United States Patent
Pratt et al.

(10) Patent No.: US 10,179,196 B2
(45) Date of Patent: Jan. 15, 2019

(54) DRESSINGS, SYSTEMS, AND METHODS FOR TREATING A WOUND ON A PATIENT'S LIMB EMPLOYING LIQUID CONTROL

(71) Applicant: KCI Licensing, Inc., San Antonio, TX (US)

(72) Inventors: Benjamin Andrew Pratt, Poole (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 266 days.

(21) Appl. No.: 15/229,422

(22) Filed: Aug. 5, 2016

(65) Prior Publication Data
US 2016/0339155 A1 Nov. 24, 2016

Related U.S. Application Data

(63) Continuation of application No. 13/674,782, filed on Nov. 12, 2012, now Pat. No. 9,433,711.
(Continued)

(51) Int. Cl.
*A61F 13/06* (2006.01)
*A61M 1/00* (2006.01)
(Continued)

(52) U.S. Cl.
CPC ....... *A61M 1/009* (2014.02); *A61F 13/00063* (2013.01); *A61F 13/00068* (2013.01); *A61F 13/00987* (2013.01); *A61F 13/022* (2013.01); *A61F 13/0216* (2013.01); *A61F 13/08* (2013.01); *A61F 13/085* (2013.01); *A61F 13/45* (2013.01); *A61F 13/8405* (2013.01); *A61M 1/0023* (2013.01); *A61M 1/0031* (2013.01);
(Continued)

(58) Field of Classification Search
CPC .............. A61F 13/022; A61F 13/00068; A61F 13/0216
See application file for complete search history.

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 145271 B2 3/2002
(Continued)

OTHER PUBLICATIONS

Japanese Application No. 2014-541376—Notice of Rejection, dated Aug. 16, 2016.
(Continued)

*Primary Examiner* — Susan Su

(57) ABSTRACT

Wound dressings, systems, and methods are presented for treating a wound on a patient's limb, such as a venous leg ulcer. The dressings, systems, and methods involve creating airflow within the dressing to vaporize and remove liquid. The airflow may begin when the dressing becomes saturated. The dressings may be used to provide compression and reduced pressure to the wound. Other systems, methods, and dressings are presented herein.

16 Claims, 7 Drawing Sheets

Related U.S. Application Data

(60) Provisional application No. 61/558,544, filed on Nov. 11, 2011.

(51) Int. Cl.
*A61F 13/45* (2006.01)
*A61F 13/00* (2006.01)
*A61F 13/02* (2006.01)
*A61F 13/08* (2006.01)
*A61F 13/84* (2006.01)

(52) U.S. Cl.
CPC ... *A61M 1/0092* (2014.02); *A61F 2013/8408* (2013.01); *A61M 2205/7536* (2013.01); *Y10T 29/49826* (2015.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower Guiles, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,381,611 A * | 5/1983 | Wishman | A42C 5/02 34/339 |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,556,055 A * | 12/1985 | Bonner, Jr. | A61F 7/10 128/DIG. 15 |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,254,554 B1 * | 7/2001 | Turtzo | A61H 9/0078 601/134 |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,142,378 B2 * | 3/2012 | Reis | A61F 5/05816 602/13 |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2004/0015115 A1 * | 1/2004 | Sinyagin | A61F 13/00987 602/42 |
| 2005/0010155 A1 * | 1/2005 | Chiang | A61F 5/01 602/60 |
| 2005/0159695 A1 * | 7/2005 | Cullen | A61L 15/28 602/48 |
| 2007/0021706 A1 * | 1/2007 | Braunstein | A61F 5/0109 602/63 |

(56) References Cited

U.S. PATENT DOCUMENTS

| | | | |
|---|---|---|---|
| 2007/0167926 A1* | 7/2007 | Blott | A61F 13/0213 604/304 |
| 2008/0177232 A1* | 7/2008 | Knighton | A61B 17/12118 604/133 |
| 2008/0249455 A1* | 10/2008 | Brown | A61H 9/0078 602/75 |
| 2009/0124944 A1 | 5/2009 | Ravikumar | |
| 2009/0227969 A1 | 9/2009 | Jaeb et al. | |
| 2010/0016815 A1* | 1/2010 | Vitaris | A61F 13/00068 604/304 |
| 2010/0082060 A1* | 4/2010 | Avitable | A61H 9/0078 606/202 |
| 2010/0185163 A1 | 7/2010 | Heagle | |
| 2010/0268128 A1 | 10/2010 | Randolph | |
| 2011/0054283 A1* | 3/2011 | Shuler | A61B 5/14539 600/364 |
| 2013/0053798 A1* | 2/2013 | Coulthard | A61F 13/00055 604/319 |
| 2013/0317406 A1* | 11/2013 | Locke | A61M 1/0001 602/46 |
| 2014/0163491 A1 | 6/2014 | Schuessler et al. | |
| 2015/0080788 A1 | 3/2015 | Blott et al. | |
| 2015/0119774 A1* | 4/2015 | Rogers | A61F 13/00068 602/3 |

FOREIGN PATENT DOCUMENTS

| | | |
|---|---|---|
| AU | 155496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp: 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., MD., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

(56) References Cited

OTHER PUBLICATIONS

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

DRESSINGS, SYSTEMS, AND METHODS FOR TREATING A WOUND ON A PATIENT'S LIMB EMPLOYING LIQUID CONTROL

RELATED APPLICATIONS

The present application is a continuation of U.S. patent application Ser. No. 13/674,782, entitled "Dressings, Systems, and Methods for Treating a Wound on a Patient's Limb Employing Liquid Control," filed Nov. 12, 2012, which claims the benefit, under 35 USC § 119(e), of the filing of U.S. Provisional Patent Application Ser. No. 61/558,544, entitled "Dressings, Systems, and Methods for Treating a Wound on a Patient's Limb Employing Liquid Control," filed Nov. 11, 2011, which is incorporated herein by reference for all purposes.

FIELD

The present disclosure relates generally to medical treatment systems suitable for use with venous leg ulcers (VLU) and, more particularly, but not by way of limitation, to dressings, systems, and methods for treating a wound on a patient's limb, e.g., a venous leg ulcer, that employs liquid control or management.

BACKGROUND

Venous leg ulcers (VLU), which are sometimes called varicose or stasis ulcers, result from damage to the valves in the veins of the legs, leading to raised venous pressure. VLUs have a multi-faceted negative effect on the health and wellbeing of patients. Physical symptoms include pain and immobility, which in turn, may lead to sleep disturbance, lack of energy, work limitations, frustration, and a lack of self-esteem.

The main treatment has been the application of compression to minimize edema or swelling. Compression treatments include wearing compression stockings, multi-layer compression wraps, or wrapping an ACE bandage or dressing from the toes or foot to the area below the knee. Other wounds may also be experienced on limbs of a patient.

SUMMARY

According to an illustrative embodiment, a wound dressing for treating a wound on a patient's limb includes a tubular sleeve member for receiving the patient's limb and a pressure source fluidly coupled to the tubular member. The tubular sleeve member includes an elastic compression member formed as a sleeve having a first side and a second, patient-facing side and a fluid-directing member having a first side and a second, patient-facing side. The first side of the fluid-directing member is disposed proximate to the second, patient-facing side of the elastic compression member. The fluid-directing member is operable to inhibit fluids from flowing through the fluid-directing member. The tubular sleeve member also includes a pathway member having a first side and a second, patient-facing side. The first side of the pathway member is proximate to the second, patient-facing side of the fluid-directing member. The pathway member is operable to transport a fluid under a pressure gradient. The pressure source is fluidly coupled to the pathway member for moving fluid therein. The wound dressing further includes at least one exhaust port fluidly coupled to the pathway member for allowing fluids to exit the wound dressing. The tubular sleeve member may also include one or more of the following: an absorbent member, a transition member, or a patient-interface member.

According to another illustrative embodiment, a dressing for treating a wound on a patient's limb includes a means for compressing the limb proximate the wound and a means for receiving liquid from the wound into the dressing. The dressing further includes a means for forcing air to flow through the dressing to facilitate vaporization and removal of liquids from the dressing.

According to another illustrative embodiment, a method for treating a wound on a patient's limb includes providing a wound dressing. The wound dressing includes a tubular sleeve member that includes an elastic compression member formed into a sleeve having a first side and a second, patient-facing side and a fluid-directing member having a first side and a second, patient-facing side. The first side of the fluid-directing member is disposed proximate to the second, patient-facing side of the elastic compression member. The fluid-directing member is operable to inhibit fluids from flowing through the fluid-directing member. The tubular sleeve member further includes a pathway member having a first side and a second, patient-facing side. The first side of the pathway member is proximate to the second, patient-facing side of the fluid-directing member. The pathway member is operable to transport a fluid under a pressure gradient. The method further includes disposing the wound dressing around the patient's limb proximate to the wound, receiving liquid from the wound into the wound dressing, and creating a pressure gradient within the wound dressing to cause air flow in the wound dressing to evaporate liquid from the wound dressing. The air enters the wound dressing at one location and is exhausted at another location.

According to another illustrative embodiment, a method of manufacturing a wound dressing for treating a wound on a patient's limb includes forming a tubular sleeve member for receiving the limb of the patient. The step of forming a tubular sleeve member includes forming an elastic compression member as a sleeve having a first side and a second, patient-facing side; forming a fluid-directing member having a first side and a second, patient-facing side; and disposing the first side of the fluid-directing member proximate to the second, patient-facing side of the elastic compression member. The fluid-directing member is operable to inhibit fluids from flowing through the fluid-directing member. The step of forming a tubular sleeve member further includes forming a pathway member having a first side and a second, patient-facing side and disposing the first side of the pathway member proximate to the second, patient-facing side of the fluid-directing member. The pathway member is operable to transport a fluid under a pressure gradient. The method of manufacturing a wound dressing further includes fluidly coupling the pressure source to the pathway member for moving fluid therein.

According to another illustrative embodiment, a system for treating a wound on a patient's limb includes a wound dressing comprising a tubular sleeve member. The tubular sleeve member includes a plurality of pressure compartments. Each pressure compartment is operable to form a pressure gradient on a portion of the patient's limb. The system further includes a pressure source that is fluidly and separately coupled to each of the pressure compartments; and a controller coupled to the pressure source to control pressure delivery to the plurality of pressure compartments. The controller and pressure source are operable to cause a first pressure compartment of the plurality of pressure compartments to compress around the patient's limb, then subsequently a second pressure compartment of the plurality of pressure compartments to compress in order to encourage fluid movement in the patient's limb from proximate the first pressure compartment towards the second pressure compartment.

According to another illustrative embodiment, a method for treating a wound on a patient's limb includes forming a plurality of pressure compartments on the patient's limb proximate the wound, sequentially compressing each pressure compartment in a cephaladic direction, and flowing air over a majority of the pressure compartments to vaporize and remove liquid.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

In treating a venous leg ulcer (VLU) or other wounds, it is desirable to apply compression, remove exudate, and control the liquid produced by the wound that is retained in a dressing. VLU's produce considerable liquids that can saturate a dressing, cause an undesirable odor, and cause maceration of healthy skin. The dressings and systems herein control the liquid from the wound in a way to avoid one or more of these conditions.

Figure 1:
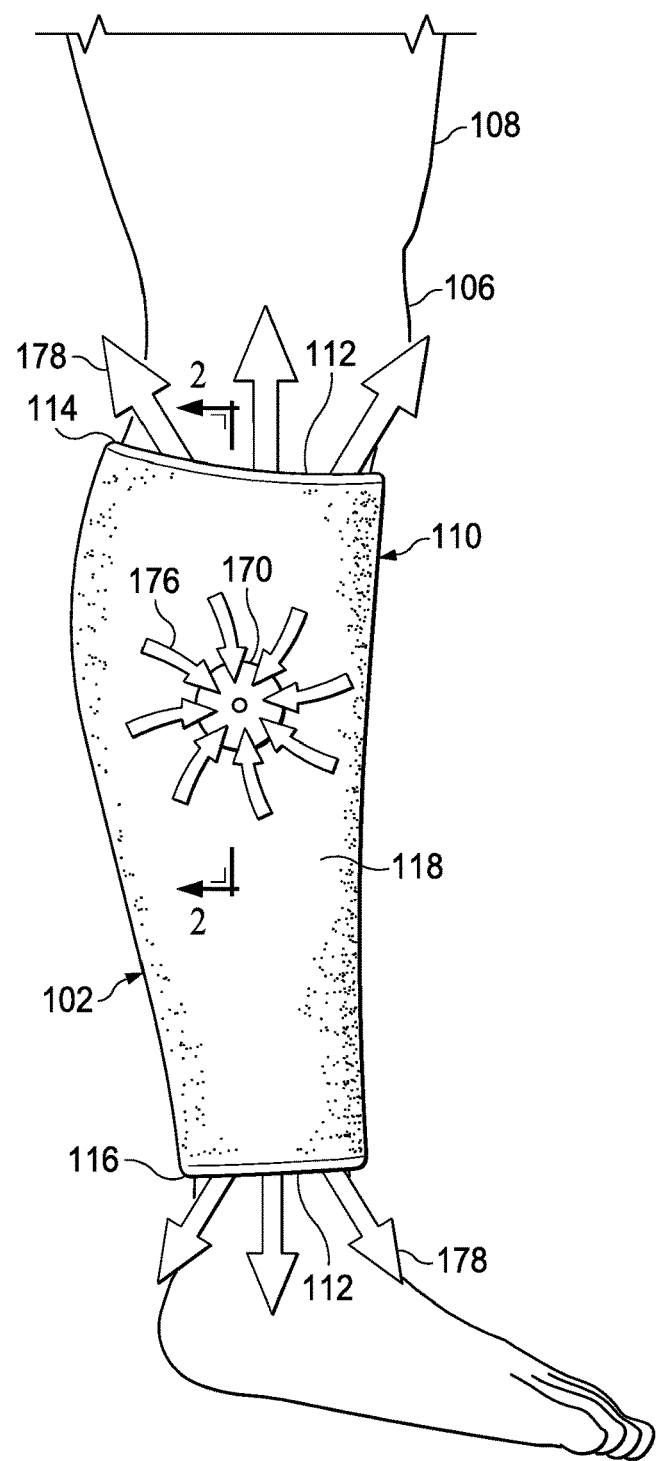
FIG. 1 is an elevation view of an illustrative embodiment of a dressing for treating a venous leg ulcer or other wound on a patient.
Figure 2:
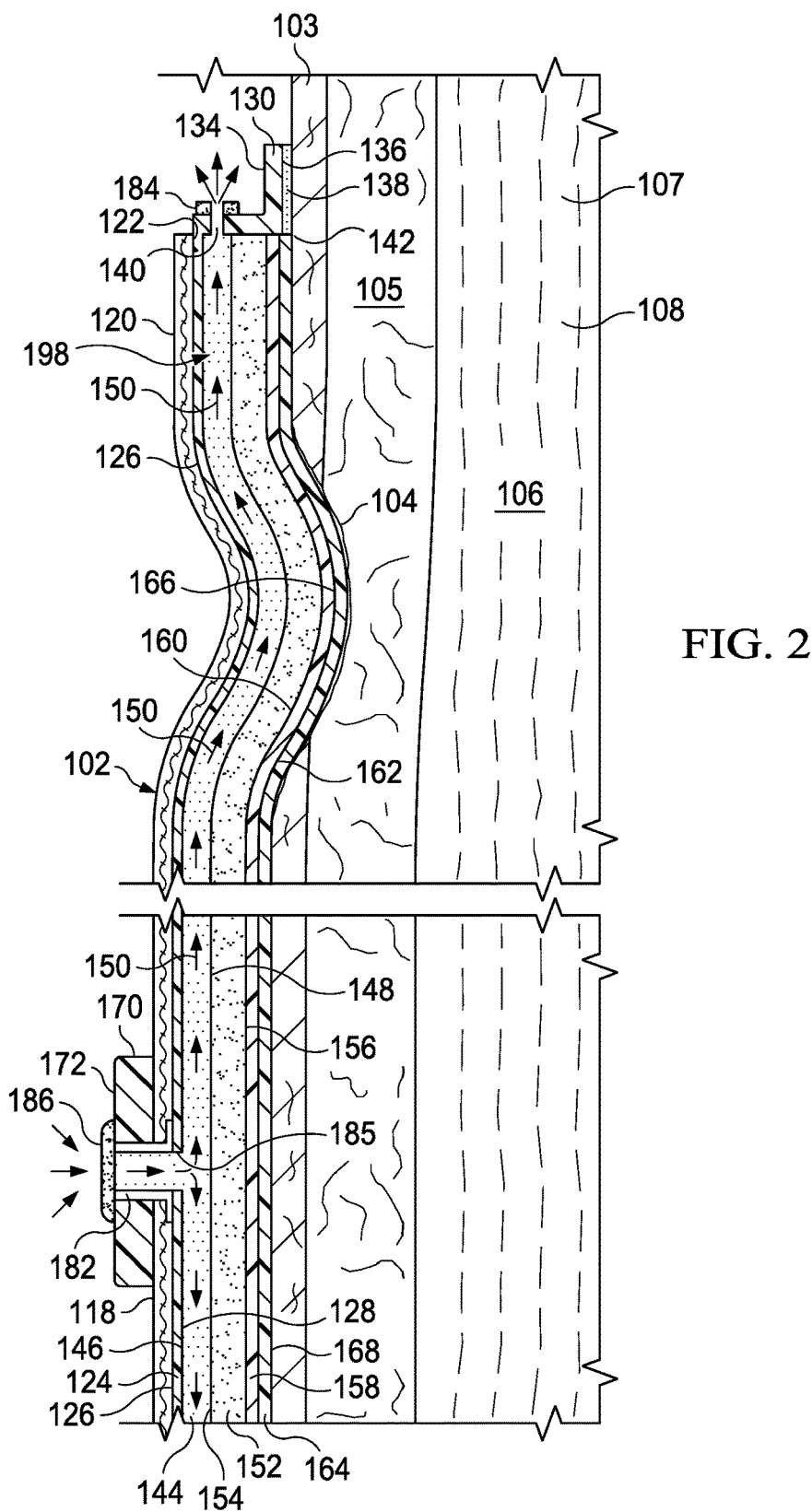
FIG. 2 is a cross section (medial) of the dressing of FIG. 1 taken along line 2-2.

Referring to the figures, and initially to FIGS. 1-2, a dressing 102 for treating a wound 104, such as a venous leg ulcer, on a limb 106 or extremity of a patient 108 is presented. The wound 104 may involve epidermis 103, dermis 105, and subcutaneous tissue 107. The dressing 102 reduces the amount of liquid from the wound 104 that is retained within the dressing 102 by using air movement to vaporize and remove fluids. The dressing 102 may reduce odor and may facilitate an overall smaller size dressing than might otherwise be possible. The dressing 102 may have a longer use time than otherwise possible.

The dressing 102 includes a tubular sleeve member 110 for receiving the limb 106 or extremity of the patient 108. The tubular sleeve member 110 has limb openings 112: a first limb opening 114 and a second limb opening 116. The limb openings 112 allow the tubular sleeve member 110 to receive the limb 106 therein. The tubular sleeve member 110 and the limb openings 112 may be sized to accommodate different sized limbs 106.

The tubular sleeve member 110 may include an elastic compression member 118 formed as a sleeve. The elastic compression member 118 is the outermost (furthest from patient 108) member of the tubular sleeve member 110. The elastic compression member 118 has a first side 120 and a second, patient-facing side 122. The elastic compression member 118 may be formed from one or more of the following materials: Nylon Powernet material; Velband; materials with combinations of relatively non-elastic nylon fibers and highly-elastic fibers (e.g., Spandex, Elastene); Lycra materials, stretch cotton; rubber materials; urethanes; silicones; or other stretch based materials. The elastic compression member 118 is optional in that an embodiment may be used as a dressing without this layer. In such a case, the next layer, a fluid-directing member 124, may securely hold the dressing 102 in place.

The tubular sleeve member 110 also includes the fluid-directing member 124. The fluid-directing member 124 has a first side 126 and a second, patient-facing side 128. The first side 126 of the fluid-directing member 124 is disposed proximate to the second, patient-facing side 122 of the elastic compression member 118. The fluid-directing member 124 is operable to inhibit fluids from flowing through the fluid-directing member 124. The fluid-directing member may comprise one or more of the following: a polyurethane (PU) drape; an elastomer (e.g., natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, EVA film, co-polyester, and silicones; silicone drape material; a 3M Tegaderm® drape; or a polyurethane (PU) drape. The fluid-directing member 124 directs fluids so that airflow is primarily out of the exhaust ports.

At the limb openings 112, the fluid-directing member 124 may extend beyond any other layers to form an extension 130. The extension 130 forms a seal with the patient's epidermis 103 as shown best in FIG. 2. The extension 130 has a first side 134 and a second, patient-facing side 136. An adhesive 138 is applied to the second, patient-facing side 136 of the extension 130 to facilitate attachment to the patient's epidermis 103. A port 140, which depending on mode of operation is an intake port or an exhaust port, is formed through the fluid-directing member 124 and any other members as necessary to access air beyond the wound dressing 102. The port 140 allows fluid to enter or exit the wound dressing 102.

Figure 3:
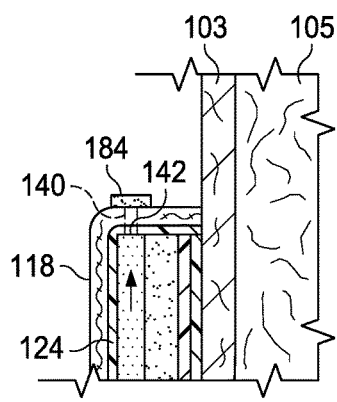
FIG. 3 is a cross section of a portion of an illustrative embodiment of a wound dressing for treating a wound, such as a venous leg ulcer, that shows another seal against a patient's epidermis.

As shown in FIG. 3, in another illustrative embodiment, the elastic compression member 118 and fluid-directing member 124 both extend over transverse edges 142 and, because of compression, impinge upon the epidermis 103 to form a seal. In this embodiment, the port 140 extends through both the elastic compression member 118 and fluid-directing member 124. In still another embodiment, all the layers may be coterminous and the entire edge may serve to exhaust vapor.

Referring again primarily to FIG. 2, the tubular sleeve member 110 further includes a pathway member 144. The pathway member 144 has a first side 146 and a second, patient-facing side 148. The first side 146 of the pathway member 144 is proximate to the second, patient-facing side 128 of the fluid-directing member 124. The pathway member 144 is operable to transport a fluid under a pressure gradient. The pathway member 144 functions to present pathways that allow a gas to flow and has sufficient rigidity to allow pathways to remain open even when compressed during use. The pathway member 144 may comprise one or more of the following: open-cell foam; non-woven material (e.g., Libeltex Hydrophobic non-woven); or Vilmed range from Freudenberg 1522. As suggested by arrows 150 in FIG. 2, air moves within the pathway member 144. Arrows 150 show airflow in one direction, but another direction is possible as is explained elsewhere.

The tubular sleeve member 110 may optionally include an absorbent member 152. The absorbent member 152 at least temporarily retains liquids from the wound 104 away from the patient's epidermis 103. The absorbent member 152 has a first side 154 and a second, patient-facing side 156. The first side 154 of the absorbent member 152 is proximate to the second, patient-facing side 148 of the pathway member 144. The absorbent member 152 acts as a buffer to hold liquid from the wound 104 while waiting for the liquid to be evaporated and carried away by airflow in the pathway member 144. The absorbent member 152 may be any material that functions to hold liquid. The absorbent member 152 may be formed from one or more of the following: a super absorbent polymer material (e.g., LUQUAFLEECE from BASF), Vilmed range from Freudenberg 1522, or other material.

The tubular sleeve member 110 may optionally include a transition member 158. The transition member 158 may be formed from the same materials as the pathway member 144. The transition member 158 has a first side 160 and a second, patient-facing side 162. The first side 160 of the transition member 158 is disposed proximate to the second, patient-facing side 156 of the absorbent member 152. The transition member 158 wicks liquids from the wound 104 to help keep fluids away from the epidermis 103 or wound 104.

The tubular sleeve member 110 may optionally include a patient-interface member 164 that has a first side 166 and a second, patient-facing side 168. The first side 166 of the patient-interface member 164 is disposed proximate to the second, patient-facing side 162 of the transition member 158 or the second, patient-facing side 156 of the absorbent member 152. The second, patient-facing side 168 of the patient-interface member 164 is for disposing proximate to the patient 108. The patient-interface member 164 is designed to be against the epidermis 103 for extended periods of time and may include an anti-microbial material, e.g., silver. The patient-interface member 164 may be formed from a Silver Miliken or other material.

Figure 10:
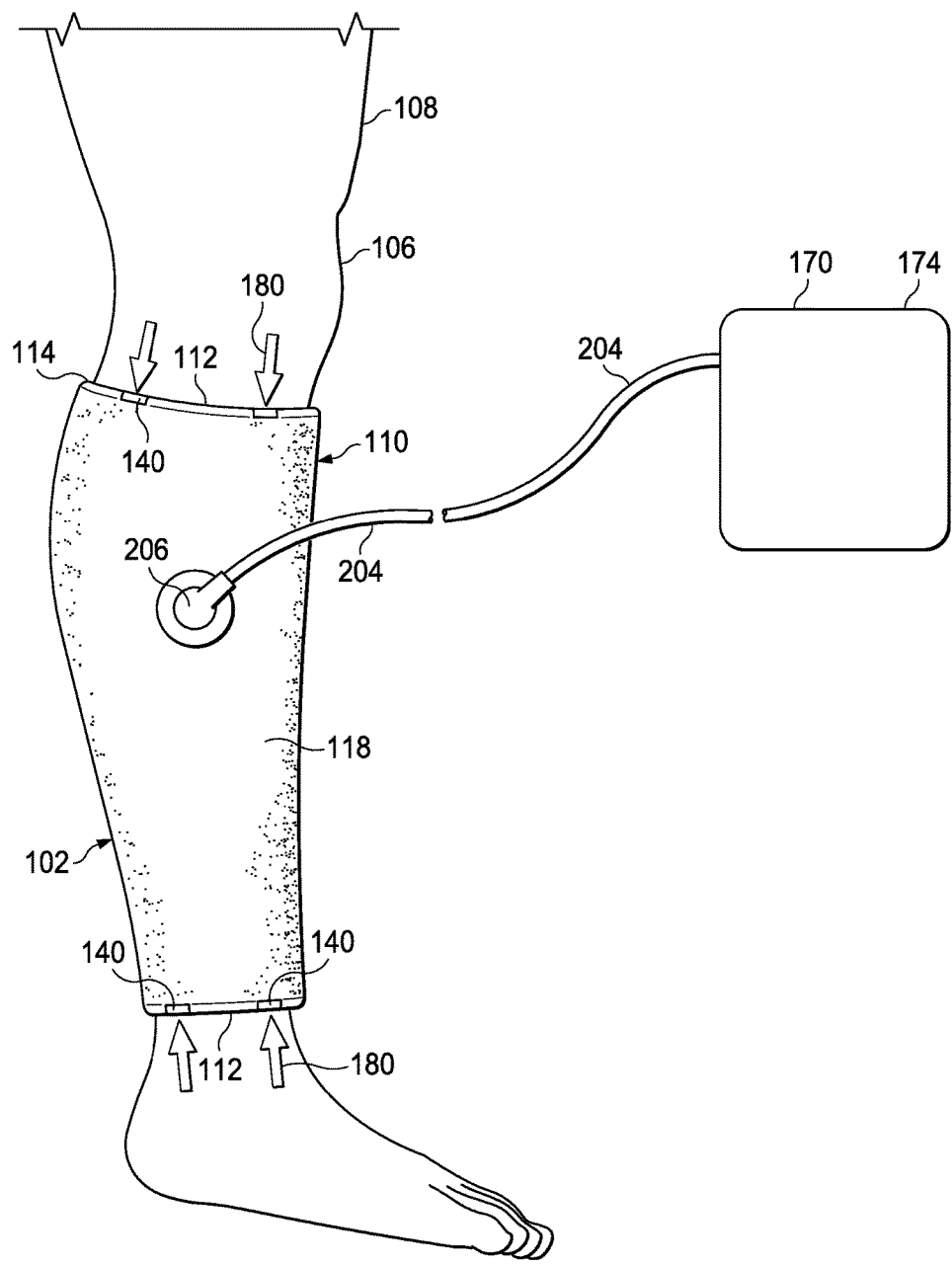
FIG. 10 is an elevation view of an illustrative embodiment of a dressing for treating a wound, such as venous leg ulcer, on a patient.

A pressure source 170 is fluidly coupled to the tubular sleeve member 110. The pressure source 170 may be, for example, a reduced-pressure source or a positive pressure source. Thus, the pressure source 170 may be a micro-pump 172 as shown in FIG. 2, a remote reduced-pressure source 174 as shown in FIG. 10, a wall-based suction source, or a wall-based positive pressure source.

As suggested by arrows 176 in FIG. 1, the pressure source 170 may be configured to pull air into the wound dressing 102 at an inboard location. The wound dressing 102 may be configured to discharge the air at the edges. The air is discharged through one port 140 at the limb opening 112 as suggested by arrows 178. Alternatively, the pressure source 170 may be configured to pull air as suggested by arrows 180 in FIG. 10 from the limb openings 112 to the pressure source 170 and then exhaust the air at the reduced-pressure source 174.

Figure 4:
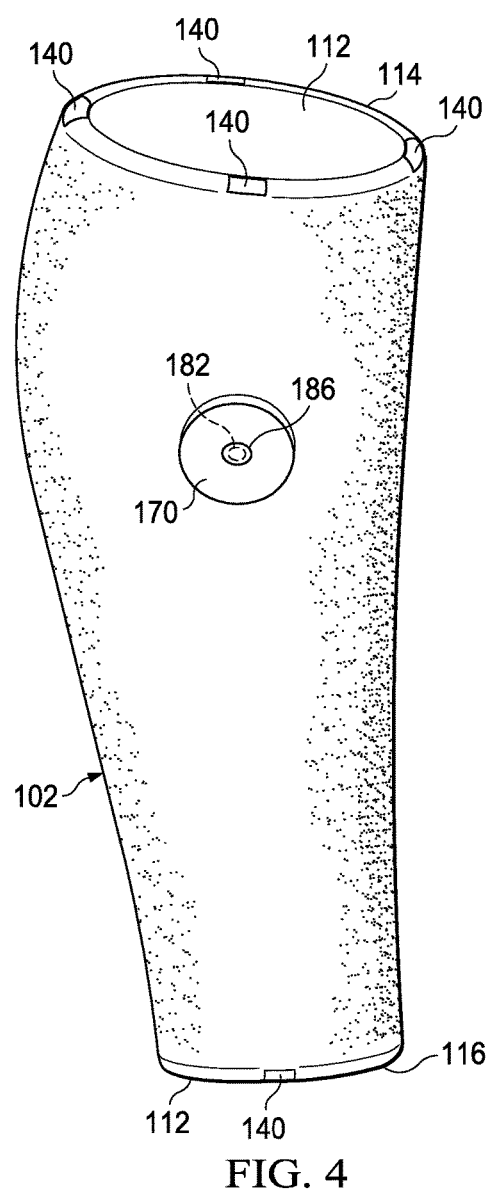
FIG. 4 is a perspective view of an illustrative embodiment of a dressing for treating a wound, such as venous leg ulcer or other wound.

The wound dressing 102 includes at least two ports: port 140 and port 182. The limb openings 112 typically include at least one port 140. As shown best in FIG. 4, a plurality of ports 140 may be included. The port or ports 140 may function as exhaust ports or intake ports depending on the configuration of the pressure source 170. Thus, in FIGS. 1-2, the port 140 is an exhaust port. In FIG. 10, the ports 140 are intake ports. The port 182 is associated with the pressure source 170 and may include an extension portion 185 to provide fluid communication with a desired layer of the wound dressing 102. For example, the extension portion 185 may fluidly couple the pressure source 170 to the pathway member 144 as shown in FIG. 2 or to another layer if desired.

The pressure source 170 causes a pressure gradient in the wound dressing 102 that will move air. Depending on how the wound dressing 102 is configured, air either enters at the edges (e.g., at the limb opening 112) and moves to port 182 or enters at the port 182 and moves to the limb opening 112 and out ports 140. The ports 140 and 182 may both may be inboard if a compartment wall is used as is described elsewhere herein. The pressure gradient is typically established primarily in the pathway member 144, but may be established in other layers in some embodiments.

Each port 140, 182 may have a filter associated with the port 140, 182. For example, a filter 184 is associated with port 140, and a filter 186 is associated with port 182. The filters 184, 186 may be odor filters, e.g., charcoal filters, or anti-bacterial filters. In FIG. 2, the filter 184 is a charcoal filter for removing odor from the airflow before the airflow is released into the atmosphere. The filter 186 is an intake filter for removing bacteria before the air enters the wound dressings 102. In FIG. 10, the intake filters (not explicitly shown) associated with ports 140 are anti-bacterial intake filters.

Figure 5:
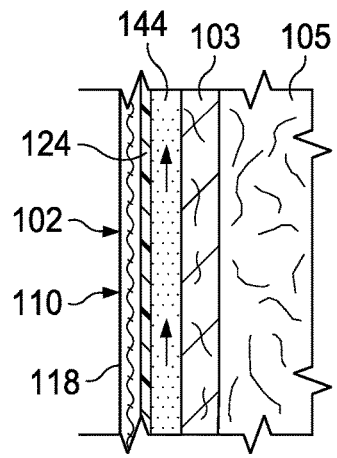
FIG. 5 is a cross section of a portion of another illustrative embodiment of a dressing for treating a wound, such as venous leg ulcer.
Figure 6:
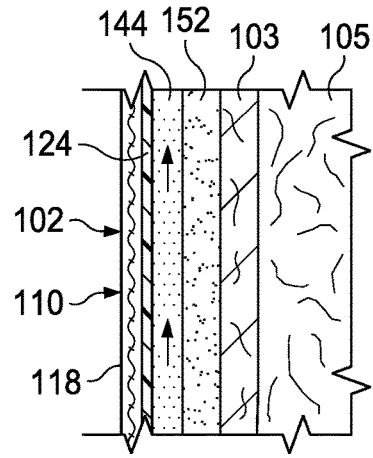
FIG. 6 is a cross section of a portion of another illustrative embodiment of a dressing for treating a wound, such as venous leg ulcer.
Figure 7:
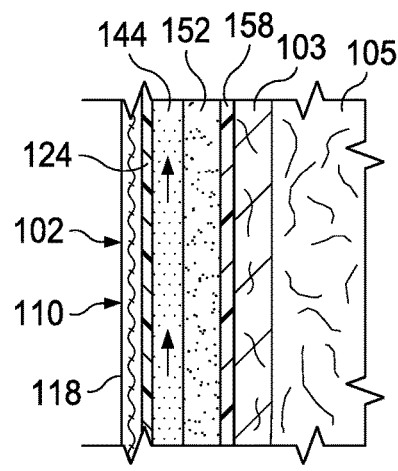
FIG. 7 is a cross section of a portion of another illustrative embodiment of a dressing for treating a wound, such as venous leg ulcer.
Figure 8:
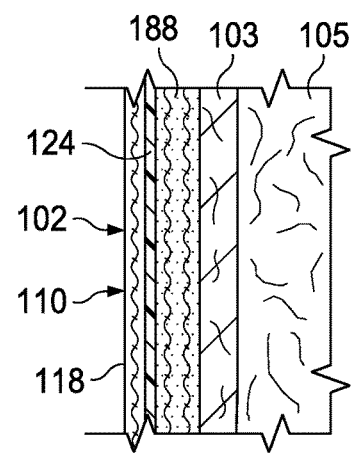
FIG. 8 is a cross section of a portion of another illustrative embodiment of a dressing for treating a wound, such as venous leg ulcer.

Of the various layers mentioned (e.g., elastic compression member 118, fluid-directing member 124, pathway member 144, absorbent member 152, transition member 158, and patient-interface member 164), some may be omitted, some combined, and some rearranged. As a few non-exhaustive examples, consider the embodiments of FIGS. 5-8. In FIG. 5, the tubular sleeve member 110 of the wound dressing 102 comprises only an elastic compression member 118, a fluid-directing member 124, and pathway member 144. In FIG. 6, the tubular sleeve member 110 of the wound dressing 102 comprises an elastic compression member 118, a fluid-directing member 124, pathway member 144, and an absorbent member 152. In FIG. 7, the tubular sleeve member 110 of the wound dressing 102 comprises an elastic compression member 118, a fluid-directing member 124, pathway member 144, an absorbent member 152, and a transition member 158. In FIG. 8, the tubular sleeve member 110 of the wound dressing 102 comprises an elastic compression member 118, a fluid-directing member 124, and a woven-open-structure member 188. The woven-open-structure member 188 functionally combines the pathway member 144, absorbent member 152, and the transition member 158 into one material. The woven-open-structure member 188 is operable to retain fluids and at the same time allow gases to move in the woven-open-structure member 188. The woven-open-structure member 188 may be formed from Vilmed range from Freundenberg 1522 or other similar material, for example.

Figure 9:
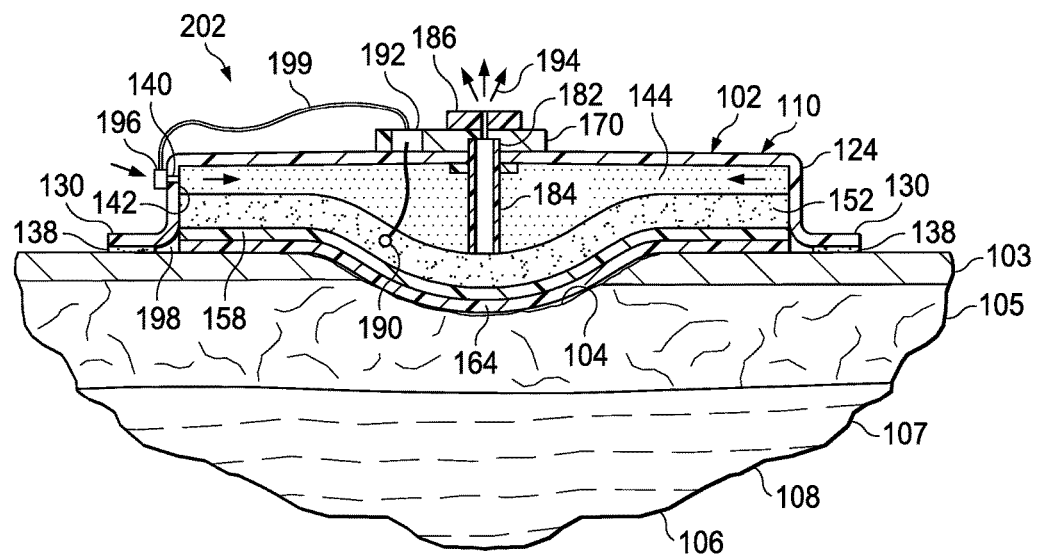
FIG. 9 is a cross section of another illustrative embodiment of a dressing for treating a wound, such as venous leg ulcer.

Referring now to FIG. 9, another illustrative embodiment of a wound dressing 102 for treating a wound 104 on a limb 106 of a patient 108 is presented. The cross section is a medial cross section of the limb 106 with the wound dressing 102 applied thereto. The wound dressing 102 is analogous in most respects to the wound dressing of FIGS. 1-2, except the elastic compression member 118 is omitted and additional features added as will be explained. The wound dressing 102 may be formed as an annular sleeve, as an isolated dressing, or island dressing. The wound dressing 102 may be used with or without compression. If compression is desired, the compression is developed by application of the fluid-directing member 124 in tension. The wound dressing 102 is held by adhesive 138 to the patient 108.

In this embodiment, a control subsystem 202 is included. The control subsystem 202 includes at least one saturation sensor 190. The saturation sensor 190 is coupled to the absorbent member 152. In other embodiments, the saturation sensor 190 may be coupled to other layers, e.g., the transition member 158. The saturation sensor 190 may be a galvanic cell with two electrodes that produce voltage when saturated, a resistive pathway that is completed by exudate, or a capacitor-based sensor.

The saturation sensor 190 is coupled to a control circuit or controller 192. The controller 192 is configured to monitor the saturation sensor 190. When the controller 192 detects a change indicative that the absorbent member 152 is saturated or partially saturated, the controller 192 activates the pressure source 170 in response. The pressure source in this embodiment pulls gas from the port 182 and discharges the gas to the atmosphere as suggested by arrows 194. The air is pulled from the transverse edges 142 through one or more ports 140. In this embodiment, the ports 140 may have a control valve 196 associated with each port 140. The control valve 196 may be wirelessly or electrically coupled by a lead 199 to the controller 192. The control valve 196 regulates air flow through the one or more ports 140 to keep air moving in the wound dressing 102, but also to control the rate such that, if desired, a reduced pressure may be maintained in a sealed space 198 at a desired level.

As an alternative to the control valve 196, controlled leaks in the fluid-directing member 124 may be used. The controlled leaks allow air to flow in at or near the transverse edges 142 towards the pressure source 170. For example, apertures (not explicitly shown) in the fluid-directing member 124 may be covered by an adhesive film that is removed later when a leak is desired.

Figure 11:
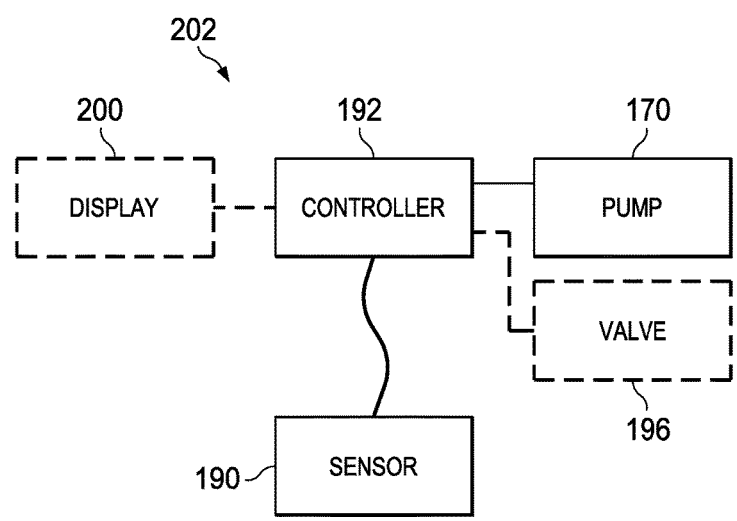
FIG. 11 is a schematic diagram of a control subsystem for use with a dressing for treating a wound, such as venous leg ulcer.

With the embodiment of FIG. 9, a reduced pressure may be applied to the wound 104 and liquids removed and managed. The reduced pressure is initially applied by the pressure source 170. When sufficient liquids reach the absorbent member 152 and saturate the absorbent member 152, the control valve 196 may be at least partially opened to allow some fluid flow into the wound dressing 102 and at the same time the pressure source 170 may be sufficiently increased to hold the desired reduced pressure notwithstanding the introduction of air through ports 140. As shown in the diagram of FIG. 11, a display 200 may be added to the control subsystem 202 to provide feedback to a user. The display 200 may be a series of LED indicators, a bi-stable LCD type, or other compact display. The display 200 is compact and low power. The display 200 may display information such as remaining battery capacity, duration of therapy, and the fill status of the dressing as well as confirmation that the system is operating within its normal parameters.

Referring now primarily to FIG. 10, another illustrative embodiment of a wound dressing 102 for treating a wound 104 on a limb 106 of a patient 108 is presented. The wound dressing 102 is analogous to those previously presented, except in this embodiment, the pressure source 170 is a remote reduced-pressure source 174. The remote reduced-pressure source 174 is fluidly coupled by a pressure conduit 204 to the tubular sleeve member 110. A pressure interface 206 may be used to fluidly couple the pressure conduit 204 to the intake port (see port 182 in FIG. 2). The intake port is at an inboard location on the wound dressing 102. In one illustrative embodiment, the pressure interface 206 is a T.R.A.C.® Pad or Sensa T.R.A.C.® Pad available from KCI of San Antonio, Tex., or another interface. In another embodiment, a "bridge" (an open-cell foam or other passageway material enclosed in a gas-impermeable material) is used to deliver reduced pressure to the wound dressing 102.

Referring now primarily to FIG. 11, the control subsystem 202 includes a controller 192 that is coupled to a saturation sensor 190 and to a pressure source 170. In addition, a control valve 196 may be coupled to the controller 192 and also a display 200. The control subsystem 202 may control the leak rate by opening the control valve 196 when included or may turn on, turn off, increase, or decrease the pressure produced by the pressure source 170. As used through out this document, "or" does not require mutual exclusivity. The control valve 196 may be a solenoid valve such a Pneutronics X valve with a fixed size orifice from Parker Hannifin, Cleveland, Ohio; a mechanical proportional valve; or a PZT proportional valve such as those supplied by Festo.

It should be understood that the control subsystem 202 of FIG. 11 or aspects of the control subsystem 202 may be applied to any of the embodiments herein. Thus, for example, when the control subsystem 202 is added to the wound dressing 102 in FIGS. 1-2, the saturation sensor 190 and controller 192 determine when the absorbent member 152 is saturated or partially saturated. The controller 192 may then activate the pressure source 170 to initiate airflow in the wound dressing 102 to evaporate and remove liquids from the wound dressing 102. The sensor 109 and controller 192 may detect saturation as a scale. The duration of the airflow or the speed of the airflow may be set by the controller 192 in response to the degree of saturation involved. The control system 202 may also display information such as remaining battery capacity, duration of therapy, and the fill status of the dressing as well as confirmation that the system is operating within its normal parameters.

Figure 12:
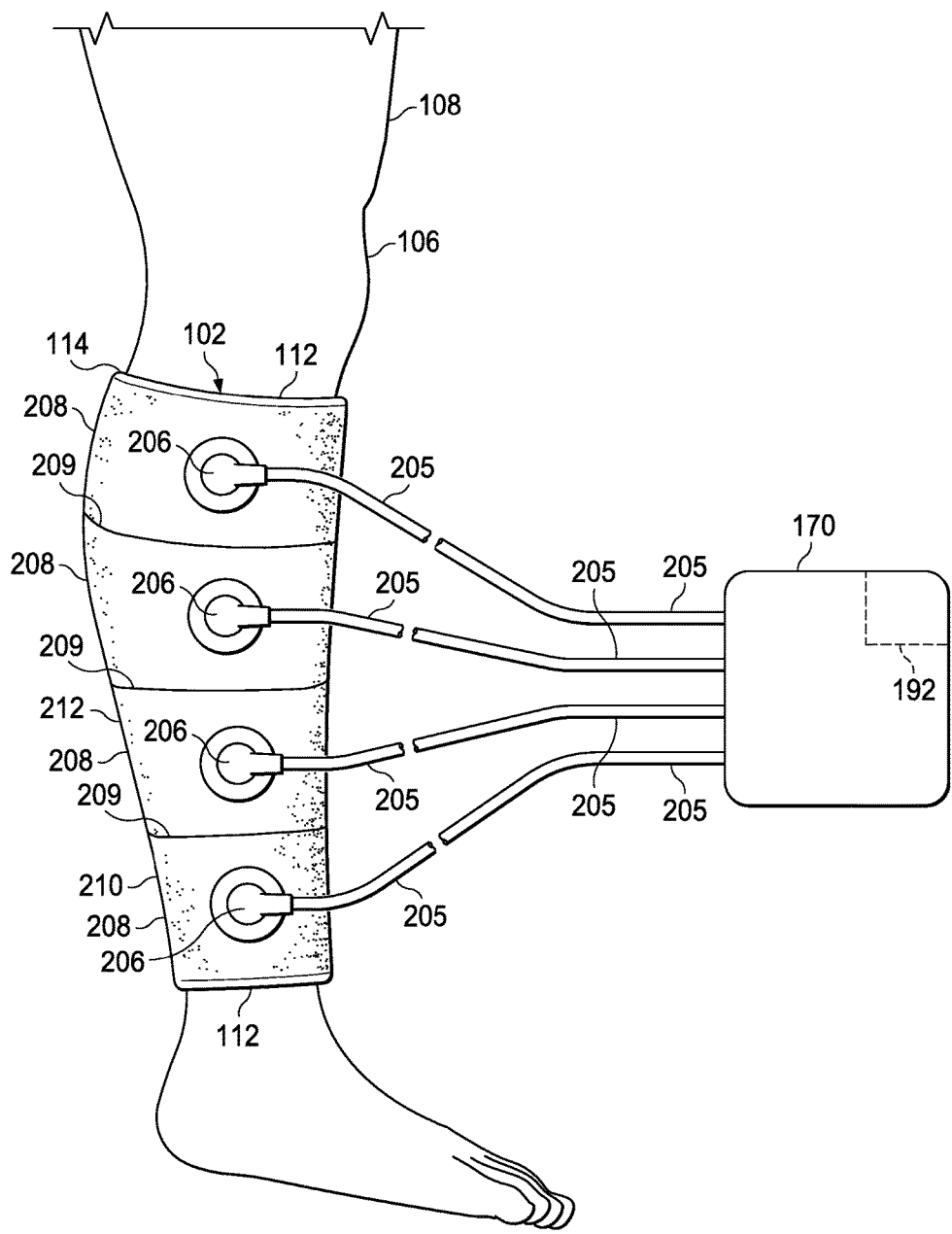
FIG. 12 is an elevation view of another dressing for treating a wound, such as venous leg ulcer, on a patient.

Referring now primarily to FIG. 12, another illustrative embodiment of a wound dressing 102 is presented. The wound dressing 102 is analogous in most respects to the previously presented wound dressings, except in this embodiment, a plurality of pressure compartments 208 are added and are used to massage the limb 106. Each pressure compartment 208 is operable to form a pressure gradient on a portion of the patient's limb 106 to move air for the purposes previously presented. In addition, the pressure compartments 208, which are formed with a plurality of compartment walls 209, allow squeezing or sequenced movement in a cephaladic direction.

A pressure source 170 is fluidly coupled separately to each of the pressure compartments 208 by a plurality of pressure conduits 205. Each pressure compartment 208 has a pressure interface 206 for fluidly coupling the pressure conduit 205 to the pressure compartment 208. Each pressure conduit 205 is also fluidly coupled to the pressure source 170.

A controller 192 is coupled to the pressure source 170 to control pressure delivery to the plurality of pressure compartments 208. The controller 192 and pressure source 170 are operable to cause a first pressure compartment 210 of the plurality of pressure compartments 208 to compress around the patient's limb 106, then subsequently a second pressure compartment 212 of the plurality of pressure compartments 208 to compress around the patient's limb 106 in order to encourage fluid movement in the patient's limb 106 from proximate the first pressure compartment 210 towards the second pressure compartment 212. The coordinated compression of pressure compartments 208 may continue with the others.

The pressure source 170 may have a controller 192 associated with the pressure source 170. The controller 192 may be configured to control a plurality of pumps within the pressure source 170 or a plurality of valves (not explicitly shown) to allow varying pressure within the pressure compartments 208. The controller 192 can sequentially supply a pressure gradient to the pressure compartments 208 to cause sequential compression of the compartments on the patient's limb 106. The sequential compression of each pressure compartment results in moving fluids in the patient's limb in a cephaladic direction (in the direction that goes from the feet towards the head). This motion thus creates a massage like motion on the limb 106. At the same time, as with the previous embodiments, air flow may be introduced into the wound dressing 102 to facilitate evaporation and removal of liquids.

The compression of each pressure compartment 208 may be achieved using positive pressure or reduced pressure from the pressure source 170. If positive pressure is used, the pressure compartments 208 may include bladders that fill to cause compression. If reduced pressure is used, the reduced pressure may cause the fluid-directing member 124 to pull down on the other layers which act as a bolster and thereby generate a compressive force.

With reference generally to the figures, in operation according to one illustrative embodiment, a wound dressing 102 is provided. The wound dressing 102 may be any of those presented or suggested herein or combinations thereof. The wound dressing 102 includes a tubular sleeve member 110. The wound dressing 102 is disposed around the patient's limb 106 proximate to the wound 104. This may entail sliding the patient's limb 106 through the limb openings 112 or using an open and closeable seam (not explicitly shown).

Once the wound dressing 102 is in place on the limb 106, the wound dressing 102 may receive liquid from the wound 104 into the wound dressing 102. Either all the time, in response to saturation or partial saturation, or based on a timer, the pressure source 170 is activated. The pressure source 170 creates a pressure gradient within the wound dressing 102 that causes air flow in the wound dressing 102 to evaporate liquid from the wound dressing 102. The air enters the wound dressing 102 at one location (e.g., port 182 or port 140) and is exhausted at another location (e.g., port 140 or 182).

The air typically will travel within the wound dressing 102 at a rate of at least 0.1 m/s and is typically in the range 0.01 (or less) to 0.2 m/s. If a saturation sensor 190 and controller 192 are included, they may detect when the saturation has dropped below a threshold level and then signal the pressure source 170 to cease. With spaced intake and exhaust ports, the air will flow over a large portion of the interior of the wound dressing 102. For example, the air may flow over 50 percent, 75 percent, 90% percent or more of the surface area of the pathway member 144 (or other layer if coupled to another layer).

In operation according to another illustrative embodiment, reduced pressure may also be applied to the wound 104 as an aspect of treatment. For example, with respect to FIG. 9, the control valve 196 may remain closed or restricted while reduced pressure is applied to the sealed space 198 to allow the creation of reduced pressure in the sealed space 198. The pressure may be, for example, without limitation, in the −25 mm Hg to −200 mm Hg range. If saturation is detected, the control valve 196 may be opened to allow for increased air flow. In addition, the output of the pressure source 170 may be increased to allow the reduced pressure level to be maintained in the sealed space 198 notwithstanding the leak or bleeding of air.

The air entering or exiting the wound dressing 102 through ports 140 and 182 may first go through a filter 184, 186. The filters 184, 186 remove bacteria or odor. The intake filter will keep bacteria from entering the wound dressing 102 and potentially infecting the wound 104. The exit filter helps remove particulates or remove odors. The configuration of the pressure source 170 determines whether a filter is an intake filter or exit filter.

According to another illustrative embodiment, a method of manufacturing a wound dressing 102 for treating a wound 104 on a patient's limb 106 is contemplated. The method includes forming a tubular sleeve member 110 for receiving the patient's lower extremity or limb 106. The step of forming the tubular sleeve member 110 includes forming an elastic compression member 118 as a sleeve having a first side 120 and a second, patient-facing side 122; forming a fluid-directing member 124 having a first side 126 and a second, patient-facing side 128; and disposing the first side 126 of the fluid-directing member 124 proximate to the second, patient-facing side 122 of the elastic compression member 118. The fluid-directing member 124 is operable to inhibit fluids from flowing through the fluid-directing member 124. The step of forming the tubular sleeve member 110 further includes forming a pathway member 144 having a first side 146 and a second, patient-facing side 148 and disposing the first side 146 of the pathway member 144 proximate to the second, patient-facing side 128 of the fluid-directing member 124. The pathway member 144 is operable to transport a fluid under a pressure gradient. The method further includes fluidly coupling the pressure source 170 to the pathway member 144 for moving fluid therein.

With respect to the preceding method, the step of forming a tubular sleeve member 110 may further include disposing an absorbent member 152, which is for at least temporarily retaining liquids, into the wound dressing 102. The absorbent member 152 has a first side 154 and a second, patient-facing side 156. The first side 154 of the absorbent member 152 is disposed proximate to the second, patient-facing side 148 of the pathway member 144. The step of forming a tubular sleeve member 110 may further include disposing a transition member 158 proximate to the absorbent member 152 or disposing the patient-interface member 164 into the wound dressing 102. One or more layers may be omitted and the order of the layers may be varied.

While air flow through the pathway member 144 is a prominent illustrative embodiment, it should be noted that the wound dressing 102 may be configured to accommodate air flow in others layers except the fluid-directing member 124. Thus, for example and without limitation, the extension portion 185 (FIG. 2) of the port 182 may extend to the absorbent member 152 or the transition member 158 to cause airflow primarily therein.

It should be understood that airflow may be from an inboard location to the transverse edges 142, from the transverse edges 142 to an inboard location, or from an inboard location to another inboard location. With respect to the lastly mentioned flow pattern and with general reference to FIGS. 2 and 3, an embodiment of a wound dressing 102 has the intake port and exhaust port that are both inboard of the transverse edges 142, but separated by a medial compartment wall (not shown, but analogous to compartment wall 209 in FIG. 12 and running medially). In this latter embodiment, the transverse edges 142 are sealed, air enters the intake port proximate to the compartment wall, the air transversely flows around the limb 106, and then the air exits the exhaust port proximate to the compartment wall but on the opposite side from the intake port.

The wound dressings 102 herein may require fewer changes than other wound dressings because of the liquid management, i.e., the liquid removed by the airflow. The liquid management may also avoid maceration on the patient. The wound dressings 102 may provide less odor and bulk than other dressings. The wound dressing 102 may process more liquid over time that the dressing is otherwise capable of retaining.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment. For example, the control subsystem 202 of FIG. 11 may be added to any of the other embodiments. As another example, pressure compartments 208 of FIG. 12 may be added to any of the other wound dressings 102 herein. As another example, the tubular sleeve members 110 shown in FIGS. 5-8 may be used with any of the wound dressing 102 embodiments herein.

It will be understood that the benefits and advantages described above may relate to one embodiment or may relate to several embodiments. It will further be understood that reference to "an" item refers to one or more of those items. It should be apparent that the power supply is implicitly present.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method for treating a wound on a patient's limb, the method comprising:
   providing a wound dressing, wherein the wound dressing comprises a tubular sleeve member, and wherein the tubular sleeve member comprises:
   an elastic compression member formed into a sleeve having a first side and a second, patient-facing side,
   a fluid-directing member having a first side and a second, patient-facing side, wherein the first side of the fluid-directing member is disposed proximate to the second, patient-facing side of the elastic compression member, and wherein the fluid-directing member is operable to inhibit fluids from flowing through the fluid-directing member, and
   a pathway member having a first side and a second, patient-facing side, wherein the first side of the pathway member is proximate to the second, patient-facing side of the fluid-directing member, wherein the pathway member is operable to transport a fluid under a pressure gradient;
   disposing the wound dressing around the patient's limb proximate to the wound;
   receiving liquid from the wound into the wound dressing; and
   creating a pressure gradient within the wound dressing to cause air flow in the pathway member to evaporate liquid from the wound dressing, the air enters the wound dressing at one location and is exhausted at another location.

2. The method of claim 1, wherein the step of creating a pressure gradient further comprises filtering the air flow with a charcoal filter to remove odors.

3. The method of claim 1, wherein the step of creating a pressure gradient within the wound dressing to cause air flow comprises causing air flow at a rate of at least 0.1 m/s.

4. The method of claim 1,
   wherein the tubular sleeve member further comprises an absorbent member for at least temporarily retaining liquids, the absorbent member having a first side and a second, patient-facing side, wherein the first side of the absorbent member is proximate to the second, patient-facing side of the pathway member; and
   wherein the step of receiving liquid comprises receiving liquid into the absorbent member.

5. The method of claim 4, wherein the step of creating a pressure gradient within the wound dressing to cause air flow comprises causing an air flow in the absorbent member of the wound dressing once the absorbent member is saturated.

6. The method of claim 5, wherein the step of creating a pressure gradient within the wound dressing to cause air flow further comprises stopping the air flow in response to the absorbent member no longer being saturated.

7. The method of claim 4, wherein the fluid-directing member creates a sealed space and wherein the step of creating a pressure gradient within the wound dressing comprises applying a reduced pressure in the sealed space and allowing air to enter an intake port.

8. The method of claim 4, wherein the fluid-directing member creates a sealed space and wherein the step of creating a pressure gradient within the wound dressing comprises applying a reduced pressure in the sealed space and allowing air to enter an intake port at intervals.

9. The method of claim 4, wherein the step of creating a pressure gradient within the wound dressing further comprises filtering the air with an odor filter before the air exits the wound dressing.

10. The method of claim 1,
wherein the tubular sleeve member further comprises:
an absorbent member for at least temporarily retaining liquids, the absorbent member having a first side and a second, patient-facing side, wherein the first side of the absorbent member is proximate to the second, patient-facing side of the pathway member, and
a transition member having a first side and a second, patient-facing side, wherein the first side of the transition member is disposed proximate to the second, patient-facing side of the absorbent member, the transition member wicks liquids; and
wherein the step of receiving liquid comprises receiving liquid into the transition member and to the absorbent member.

11. The method of claim 1, wherein the wound dressing has at least one port on a limb opening and wherein the step of creating a pressure gradient within the wound dressing comprises fluidly coupling a reduced-pressure source to the wound dressing at an inboard location and pulling air from the at least one port to the reduced-pressure source.

12. The method of claim 1, wherein the wound dressing has at least one port on a limb opening and wherein the step of creating a pressure gradient within the wound dressing comprises fluidly coupling a reduced-pressure source to the wound dressing at an inboard location and pushing air from the reduced-pressure source to the at least one port.

13. The method of claim 1, wherein the pathway member has a surface area, and wherein the step of creating a pressure gradient comprises causing air flow over at least 50 percent of the surface area of the pathway member.

14. The method of claim 1, wherein the pathway member has a surface area, and wherein the step of creating a pressure gradient comprises causing air flow over at least 75 percent of the surface area of the pathway member.

15. The method of claim 1, wherein the pathway member has a surface area, and wherein the step of creating a pressure gradient comprises causing air flow over at least 90 percent of the surface area of the pathway member.

16. A method for treating a wound on a patient's limb comprising:
providing a wound dressing having:
an elastic compression member having a first side and a second side forming a sleeve;
a fluid-directing member having a first side positioned adjacent the second side of the elastic compression member, a second side, and being operable to inhibit fluids from flowing through the fluid-directing member;
a pathway member having a first side positioned adjacent the second side of the fluid-directing member, a second side, and being operable to permit flow of a fluid when the wound dressing is under a pressure gradient; and
at least one exhaust port fluidly coupled to the pathway member and operable to allow fluids to exit the wound dressing;
disposing the wound dressing around the patient's limb so that the second side of the pathway member is proximate to the wound;
receiving liquid from the wound into the pathway member;
fluidly coupling a pressure source to the pathway member for generating the pressure gradient; and
operating the pressure source to create a pressure gradient between the pressure source and the at least one exhaust port through the pathway member to generate a fluid flow through the pathway member and evaporate the liquid received in the pathway member.

* * * * *